United States Patent [19]

Tabuchi et al.

[11] Patent Number: 5,650,532
[45] Date of Patent: Jul. 22, 1997

[54] ACRYLIC MONOMER

[75] Inventors: Takeharu Tabuchi, Otake; Takaaki Fujiwa, Arai; Shinji Nakano, Takatsuki; Shin-ya Yamada, Sakai, all of Japan

[73] Assignees: Nippon Paint Company, Ltd., Osaka; Daicel Chemical Industries, Ltd., Osaka-fu, both of Japan

[21] Appl. No.: 568,817

[22] Filed: Dec. 7, 1995

[30] Foreign Application Priority Data

Dec. 8, 1994 [JP] Japan .................. 6-331733
Dec. 8, 1994 [JP] Japan .................. 6-331735

[51] Int. Cl.$^6$ ........................... C07C 69/96
[52] U.S. Cl. ............. 558/276; 558/267; 558/275
[58] Field of Search .................. 558/267, 275, 558/276

[56] References Cited

U.S. PATENT DOCUMENTS 4,783,544  11/1988  Yokoshima et al. ............ 558/267
4,795,810  1/1989   Harris ........................... 528/370
5,248,805  9/1993   Boettcher et al. ............. 558/270

FOREIGN PATENT DOCUMENTS 9318070  9/1993  WIPO.

OTHER PUBLICATIONS

March, *Advanced Organic Chemistry*, 3rd ed., John Wiley & Sons, New York (1985), pp. 346, 347, 351.

*Primary Examiner*—José G. Dees
*Assistant Examiner*—Dwayne C. Jones
*Attorney, Agent, or Firm*—Millen, White, Zelano, & Branigan, P.C.

[57]  ABSTRACT

A novel acrylic monomer is produced by addition reacting a hydroxyalkyl (meth)acrylate or its lactone adduct with a cyclic alkylene carbonate, and then acylating the terminal hydroxyl group of the reaction product with a reactive derivative of a monobasic alkanoic acid or a dicarboxylic acid anhydride.

6 Claims, No Drawings

ACRYLIC MONOMER

BACKGROUND OF THE INVENTION

This invention relates to a novel acrylic monomer having an acylated hydroxyalkylene carbonate group.

Vinyl monomers having a free carboxyl group are polymerized with other comonomers for producing a variety of polymeric materials used in coating compositions, adhesives, paper or textile treating agents, crosslinking agents, anodic electrodeposition paints, molding plastics, synthetic rubber or water-absorption polymers. JP-A-60/067446 discloses a carboxyl group-containing monomer produced by the addition reaction of an ethylenically unsaturated carboxylic acid such as acrylic or methacrylic acid with a lactone. This monomer is used for improving flexibility and weatherability of the resulting polymer by copolymerizing with a fluorocarbon monomer such as chlorotrifloroethylene and another comonomer such as alkyl vinyl ether, fatty acid vinyl ester or alkyl allyl ether. However, the production of this monomer suffers from certain disadvantages. Namely, removal of unreacted carboxylic acid monomer and a strong acid catalyst such as sulfuric or p-toluenesulfonic acid from the reaction mixture can be accomplished only with difficulty and coloring of the desired monomer is unavoidable. Therefore, a need exists for a carboxyl group-containing monomer which eliminates or ameliorates the above disadvantages.

Copolymers of ethyl acrylate known as acrylic rubber are in wide use in a variety of application fields such as automobile engine parts because of their excellent heat-resistant, oil-resistant and ozone-resistant properties. Performance required for these rubber parts are becoming more stringent as engines are improved in terms of performance under more severe conditions including those for clearing air pollution problems caused by exhaust gas. Therefore, a need exists for a monomeric modifier for improving the performance of acrylic rubber and other acrylic polymers.

SUMMARY OF THE INVENTION

In the first aspect, the present invention provides an acrylic monomer of the formula I:

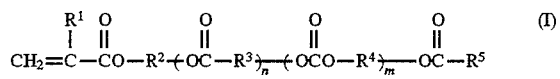
(I)

wherein $R^1$ is hydrogen or methyl, $R^2$, $R^3$ and $R^4$ are independently a $C_2$-$C_8$-alkylene bridge, $R^5$ is the residue of a monobasic $C_1$-$C_6$-alkanoic acid with removal of the carboxyl group or the residue of an aliphatic, alicyclic or aromatic dicarboxylic acid with removal of one of the carboxyl groups, n is zero or an integer of from 1 to 6, and m is an integer of from 1 to 6.

In the second aspect, the present invention provides a method for producing the acrylic monomer of the above formula I, which comprises reacting a hydroxyl group-containing monomer of the formula II:

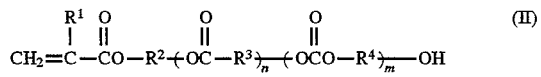
(II)

wherein all symbols are as defined, with a reactive derivative of a $C_1$-$C_6$ alkanoic acid or an aliphatic, alicyclic or aromatic dicarboxylic acid anhydride.

DETAILED DESCRIPTION OF THE INVENTION

The hydroxyl group-containing acrylic monomer of the formula II may be produced as disclosed in EP-A-0600417 by reacting a hydroxyalkyl (meth)acrylate or its lactone adduct of the formula III:

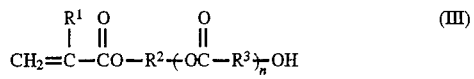
(III)

wherein $R^1$, $R^2$, $R^3$ and n are as defined, with a cyclic alkylenecarbonate of the formula IV:

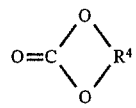

wherein $R^4$ is as defined, in the presence of a catalyst.

Examples of the starting hydroxyalkyl(meth)acrylates include 2-hydroxyethyl(meth)acrylate, 2-hydroxypropyl (meth)acrylate, 3-hydroxypropyl(meth)acrylate, and 4-hydroxybutyl(meth)acrylate. The lactone adducts are produced by the ring opening addition reaction of a $C_3$-$C_9$-alkanoic lactone such as ε-caprolactone with a hydroxyalkyl (meth)acrylate. Adducts of 2-hydroxyethyl (meth)acrylate with ε-caprolactone are commercially available from Daicel Chemical Industries, Ltd. as PCL-FA and PCL-FM series.

The cyclic alkylenecarbonate may be produced by reacting a glycol and a dialkyl carbonate followed by depolymerizing the resulting polymer as taught in JP-A-02/56356. Alternatively, the cyclic carbonate may be produced by reacting a corresponding alkylene oxide with carbon dioxide. The cyclic carbonate may form a 5–7 membered ring. Specific examples thereof include ethylene carbonate as 5-membered cyclic carbonate, 1,3-propylene carbonate and neopentyl glycol carbonate otherwise named dimethyltrimethylene carbonate as 6-membered cyclic carbonate, and 1,4-butanediol carbonate as 7-membered cyclic carbonate. Neopentyl glycol carbonate is preferable because this compound may be synthesized in relatively short steps from commercially available raw materials. Moreover, this compound is normally stable but may react with hydroxyalkyl (meth)acrylates or their lactone adducts under relatively mild conditions.

The molar ratio of the cyclic carbonate to the hydroxyalkyl (meth)acrylate or lactone adduct thereof is at least 0.5 and preferably from 1 to 6. At the molar ratio of 2 or more, successive addition polymerization of the cyclic carbonate will take place.

Examples of catalysts include organic and inorganic tin compounds such as dibutyltin oxide, dibutyltin dilaurate, monobutyltin trichloride, hydroxybutyltin oxide, stannous chloride, stannous bromide or stannous iodide; and tungsten compounds such as phosphotungstic acid or silicotungstic acid. Also included as usable catalysts are strongly acidic ion exchange resins such as Amberlist 15; and Bronsted acids such as hydrogen fluoride, hydrogen chloride, hydrogen bromide, sulfuric acid, p-toluenesulfonic acid, dodecylbenzenesulfonic acid, methanesulfonic acid, trifluoroacetic acid or trifluoromethanesulfonic acid; and Bronsted anion onium salts of nitrogen, sulfur, phosphorus or iodine. Typical examples of such onium salts are listed below:

(i) Quaternary ammonium salts:
N,N-dimethyl-N-benzylanilinium hexafluoroantimonate;
N,N-diethyl-N-benzylanilinium tetrafluoroborate;
N-benzylpyridinium hexafluoroantimonate;
N-benzylpyridinium triflate;
N-(4-methoxybenzyl)pyridinium hexafluoroantimonate;
N,N-diethyl-N-(4-methoxybenzyl)toluidinium hexafluoroantimonate; and N,N-dimethyl-N-(4-methoxybenzyl)toluidinium hexafluoroantimonate.

(ii) Sulfonium salts:
triphenylsulfonium tetrafluoroborate;
triphenylsulfonium hexafluoroantimonate;
triphenylsulfonium hexafluoroarsenate;
ADEKA CP-66(Asahi Denka Kogyo K.K.);
ADEKA CP-77(Asahi Denka Kogyo K.K.);
tri-(4-methoxyphenyl)sulfonium hexafluoroantimonate; and
diphenyl-(4-phenylthiophenyl)sulfonium hexafluoroantimonate.

(iii) Phosphonium salts:
ethyltriphenylphosphonium hexafluoroantimonate; and tetrabutylphosphonium hexafluoroantimonate.

(iv) Iodonium salts:
diphenyliodonium hexafluoroantimonate;
di-4-chlorophenyliodonium hexafluoroantimonate;
di-p-tolyliodonium hexafluoroantimonate; and
phenyl-(4-methoxyphenyl)iodonium hexafluoroantimonate.

Anions of the above onium salts may be replaced by other Bronsted acid anions such as acetate, propionate, octanoate, laurate, stearate, benzoate, benzenesulfonate, toluenesulfonate, dodecylbenzenesulfonate or perchlorate.

Examples of usable catalysts also include alkyl alkali metals such as n-butyllithium and s-butyllithium; alkali metal alkoxides such as Li, Na or K ethoxide, butoxide, isobutoxide, t-butoxide or octyloxide; amines such as diethylamine, triethylamine, dibutylamine, N,N-dimethylcyclohexylamine, dimethylbenzylamine, hexamethylenetetramine and 1,8-diazabicyclo [5,4,0]-7-undecene.

The amount of catalyst generally ranges between 1 ppm and 5%, preferably between 5 ppm and 5,000 ppm. When the amount of catalyst is less than 1 ppm the reaction velocity is too slow to be practical. Conversely, when the amount of catalyst is greater than 5% various side-reactions such as decarbonation or transesterification reaction will occur.

The reaction temperature is generally from room temperature to 150° C., preferably from room temperature to 80° C. At a reaction temperature below room temperature, the reaction velocity is too slow. Conversely at a temperature higher than 150° C., gelation of the reaction mixture may occur due to the polymerization of acrylic monomers. It is advantageous, therefore, to add from 0.01 to 5%, preferably from 0.05 to 1% of a polymerization inhibitor such as hydroquinone, hydroquinone monomethyl ether (MEHQ) or phenothiazine to the reaction system. The inhibitor is not practically effective at a concentration of less than 0.01% and excessive concentrations of greater than 5% may have adverse effects on the color of products also on subsequent copolymerization with comonomers such as alkyl (meth) acrylates.

The reaction may be carried out with or without solvent. Usable solvents are aprotic solvents such as toluene, xylene, methyl ethyl ketone or methyl isobutyl ketone. In order to prevent radical polymerization from occuring, it is advantageous for the reaction to be carried out with air bubbling or without any gas bubbling. Nitrogen gas bubbling can accelerate the radical polymerization. The solvent is used for the purpose of decreasing the viscosity of the reaction mixture and also for the purpose of keeping the mixture homogeneous to facilitate temperature control. The amount of solvent is generally from 5 to 80% by weight, preferaby from 10 to 50% by weight. Excessive amounts of greater than 80% may adversely affect the reaction velocity and satisfactory decrease in viscosity will not be accomplished in amounts less than 5%.

The materials are normally charged in a reaction vessel in the order of solvent, hydroxyl group-containing acrylic monomer, cyclic alkylene carbonate and catalyst followed by heating the mixture to a temperature as discussed supra. The reaction end point may be confirmed by gas chromatography. Normally, less than 1% concentration of the cyclic carbonate is regarded as the end point. It is not necessary at this stage to remove the solvent, if used. Turning now to the step of acylating the terminal hydroxyl group of the monomer of the formula II, the present invention uses as acylating agent, either a dicarboxylic acid anhydride when an carboxyl group-containing monomer is desired, or a reactive derivative of an alkanoic acid when a modifier of acrylic rubber and other acrylic copolymers is desired.

Examples of dicarboxylic acid anhydrides include aliphatic dicarboxylic acid anhydrides such as succinic anhydride or glutaric anhydride; alicyclic dicarboxylic acid anhydrides such as tetrahydrophthalic anhydride, 3- or 4-methyltetrahydrophthalic anhydride, hexahydrophthalic anhydride, 3- or 4-methylhexahydrophthalic anhydride; and aromatic dicarboxylic acid anhydrides such as phthalic anhydride.

The acylating reaction with the acid anhydride may be carried out at a temperature of 70°–150° C., preferably 80°–120° C. The reaction velocity is too slow at a temperature below 70° C. Conversely, at a temperature above 150° C. undesirable side-reactions can occur including decomposition reactions and the esterification of free carboxyl group of the monomer of the formula I with unreacted alcohol component of the formula II.

The reaction may proceed in the absence or presence of an appropriate catalyst. Examples of catalysts include metal carboxylates such as sodium acetate, potassium acetate, lead acetate or lead stearate; alkali metal hydroxides such as sodium hydroxide or potassium hydroxide; alkali metal carbonates such as sodium carbonate or potassium carbonate; alkali metal alkoxides such as sodium methoxide, sodium ethoxide, potassium methoxide or potassium ethoxide; quaternary ammonium bases such as the hydroxide of trimethylbenzylammonium, triethylbenzylammonium, tetraethylammonium or tetramethylammonium; and amines such as pyridine, triethylenediamine or triethylamine. Acid catalysts such as sulfuric acid or p-toluenesulfonic acid are not preferable because the acid catalyst often promotes both the main reaction and the esterifying reaction of the carboxylic acid monomer with unreacted hydroxyl group-containing monomer.

The reaction may be carried out in the absence or presence of an inert solvent such as toluene or xylene for decreasing the viscosity of reaction mixture and also for facilitating temperature control. The use of solvent will depend upon the intended use of the carboxyl group-containing acrylic monomer of the present invention. For example, the presence of a solvent is tolerated when the intended use of the monomer is for the production of vehicle resins of coating compositions. The solvent may be subsequently added to the monomer. The amount of solvent is generally from 5 to 80% by weight, preferably from 10 to 50% by weight.

The acrylic monomer of the formula I having a free carboxyl group finds use, for example, in the production of polymers for coating compositions for improving flexibility and adhesion of coating films and also for imparting the polymer with hydrophilicity and ionizable groups.

When a modifier of acrylic rubber or other acrylic copolymer is desired, the hydroxyl group-containing monomer of the formula II is acylated with a reactive derivative of a monobasic alkanoic acid such as formic, acetic, propionic, butyric, valetic or caproic acid. Reactive derivatives are acid halides such as acetyl chloride and acid anhydrides such as acetic anhydride, propionic anhydride, burytic anhydride or valetic anhydride. The acylation includes a transesterification reaction between the monomer of the formula II and an ester such as ethyl acetate or butyl acetate.

The acylating reaction may be carried out in the absence or presence of a catalyst. Examples of catalysts include a protonic acid such as sulfuric or p-toluenesulfonic acid; a Lewis acid such as $BF_3$, $SnCl_2$ or a complex thereof; an organic or inorganic base such as pyridine or sodium hydroxide; and ion exchange resins. The amount of catalyst will vary with the nature of particular catalysts and lies generally less than 10%, preferably less than 5% by weight of the starting materials.

The reaction is carried out at a temperature between 60° C. and 150° C., preferably between 80° C. and 140° C. The reaction velocity is too slow at a temperature below 60° C. At a temperature above 150° C., gelation of the reaction mixture can occur due to thermal polymerization of acrylic monomers. Use of solvent is advantageous to control the reaction. Ketones such as methyl ethyl ketone or methyl isobutyl ketone; aromatic hydrocarbons such as benzene, toluene or xylene; ethers and aliphatic hydrocarbons may be used for this purpose.

The product may be purified by a variety of conventional methods. In order to remove a trace amount of impurities produced as reaction by-products, it is preferable to wash the product with water. Prior to the washing, the crude reaction mixture is diluted with a solvent such as benzene, toluene, xylene, hexane, heptane, octane, ethyl acetate or butyl acetate. The volumetric ratio of water to the crude reaction mixture is from 0.1 to 10, preferably from 1 to 5. The water washing step may be preceded by washing with an aqueous solution of alkali such as sodium hydroxide, potassium hydroxide, sodium carbonate, potassium carbonate, sodium bicarbonate, potassium bicarbonate or ammonia to remove a trace amount of acid impurities. The concentration of alkali is not critical and may be chosen within a wide range. The washing with alkaline solution and subsequently with water may be carried out at a temperature from 10° C. to 90° C., preferably from 10° C. to 50° C.

After the washing step, the mixture is subjected to phase separation and the organic phase is recovered. The product may be recovered by evaporating the organic phase to remove the solvent. The evaporation may be carried out at a temperature of 50°–200° C., preferably 80°–160° C. If the boiling point of a particular solvent is not within the above temperature range, an appropriate reduced pressure may be applied. In order to prevent the polymerization of the product into a gel, it is advantageous to carry out the evaporation while blowing air or other oxygen-containing gas into the evaporator.

The acrylic monomer of the formula I acylated with a monobasic alkanoic acid finds use as an acrylic rubber modifier or in the production of acrylic copolymers for acrylic or polyurethane coating compositions.

The following examples are given for illustrative purposes only.

PRODUCTION EXAMPLE 1

A four necked 4L flask equipped with an air tube, thermometer, condenser and stirrer was charged with 630.7 g of 4-hydroxybutyl acrylate, 596.3 g of dimethyltrimethylene carbonate (DMTMC), 120.0 g (10% of charged reactants) of Amberlist 15 and 6.0 g of MEHQ. The mixture was allowed to react at 60° C. for 5 hours. The reaction was monitored by measuring residual DMTMC concentration with time using gas chromatography, and terminated when this concentration reached at 0.73%. The product is hereinafter called "Material A."

PRODUCTION EXAMPLE 2

The same flask as used in Production Example 1 was charged with 732.0 g of PCL-FM1 (2-hydroxyethyl methacrylate-ε-caprolactone (1:1) adduct sold by Daicel Chemical Industries, Ltd.), 390.3 g of DMTMC, 112.0 g (10% of charged reactants) of Amberlist 15 and 5.6 g of MEHQ. The mixture was allowed to react at 60° C. for 2 hours. The reaction was monitored by measuring residual concentration of DMTMC with time using gas chromatography, and terminated when this concentration reached at 0.85%. The product was hereinafter called "Material B."

EXAMPLE 1

A four necked 500 mL flask equipped with an air tube, thermometer, condenser and stirrer was charged with 274.2 g of Material A and 100.0 g of succinic anhydride. The mixture was allowed to react at 90° C. for 3 hours while blowing air stream. The reaction was monitored by measuring the acid number with time and terminated when the acid number reached 152.2 mgKOH/g (149.9 mgKOH/g in theory). $^1$H-NMR analysis was performed in acetone d-6 at room temperature using a spectrometer (JNM-EX270, JEOL Ltd.). Various peaks were assigned as follows:

δ 5.8–6.4 ppm, hydrogen in acrylic double bond;

δ 4.0–4.2 ppm, methylene hydrogen adjacent to oxygen;

δ 3.9 ppm, and δ 3.8 ppm, methylene hydrogen between ester and carbonate linkages;

δ 2.5–2.6 ppm, methylene hydrogen of ring opened succinic anhydride;

δ near 1.7 ppm, internal methylene hydrogen;

δ near 0.98 ppm, internal methylene hydrogen, and

δ near 2.0 ppm, acetone d-6.

In the IR spectrometry, the following absorption was observed.

3300 $cm^{-1}$ (broad), carboxyl;

1740 $cm^{-1}$ carbonate and ester linkages; and

1640 $cm^{-1}$ and 1620 $cm^{-1}$, acryl.

The above data support that the product is succinic acid half ester of 1:1 adduct of 4-hydroxybutyl acrylate and dimethyltrimethylene carbonate having a terminal hydroxyl group.

EXAMPLE 2

The same flask as used in Example 1 was charged with 374.3 g of Material B and 100 g of succinic anhydride. The mixture was allowed to react at 90° C. for 4 hours while blowing air stream. The reaction was monitored as in Example 1 and terminated when the acid number reached 123.2 mgKOH/g (118.3 mgKOH/g in theory).

EXAMPLE 3

The same flask as used in Example 1 was charged with 274.2 g of Material A and 154.2 g of hexahydrophthalic anhydride. The mixture was allowed to react at 90° C. for 4 hours while blowing air stream. The reaction was monitored as in Example 1 and terminated when the acid number reached 133.1 mgKOH/g (130.9 mgKOH/g in theory.)

EXAMPLE 4

The same flask as used in Example 1 was charged with 274.2 g of Material A and 112.3 g of acetic anhydride. The mixture was allowed to react at 90° C. for 2.5 hours while blowing air stream. The reaction was monitored as in Example 1 and terminated when the acid number reached 176.2 mgKOH/g (174.2 mgKOH/g in theory.)

After the reaction, the product was washed with water to remove unreacted acetic anhydride and acetic acid produced as a reaction by-product. A 200 g portion of the crude reaction mixture was dissolved in 200 g of ethyl acetate. This solution was washed with water four times using 400 g of water each time. After washing, ethyl acetate and a trace amount of water contained in the organic layer were removed by suction first with an aspirator (70–80 mmHg) for 1 hour and then with a vacuum pump (5–10 mmHg) for 30 minutes.

$^1$H-NMR analysis was performed in $CDCl_3$ at room temperature using a spectrometer (JNM-EX270, JEOL Ltd.) Various peaks were assigned as follows:

δ 5.6–6.4 ppm, hydrogen in acrylic double bond;

δ 4.1–4.2 ppm, methylene hydrogen adjacent to oxygen;

δ 3.9–4.0 ppm, methylene hydrogen adjacent to terminal ester linkage;

δ 3.8 ppm, methylene hydrogen adjacent to carbonate linkage;

δ 2.0 ppm, methylene hydrogen of terminal ester residue;

δ near 1.7 ppm, internal methylene hydrogen; and

δ near 1.10 ppm, internal methyl hydrogen.

In the IR spectrometry, an absorption of hydroxyl group at arround 3500 $cm^{-1}$ was observed in Material A, whereas this absorption was not observed in the product. Other absorptions were assigned as follows:

1740 $cm^{-1}$, carbonate linkage;

1720 $cm^{-1}$, ester linkage;

1620 $cm^{-1}$, and 1640 $cm^{-1}$, acryl.

The above data supports that the product is acetate ester of 1:1 adduct of 4-hydroxybutyl acrylate and dimethyltrimethylene carbonate having a terminal hydroxyl group.

EXAMPLE 5

The same flask as used in Example 1 was charged with 374.3 g of Material B and 112.3 g of acetic anhydride. The mixture was allowed to react at 90° C. for 3 hours while blowing air stream. The reaction was monitored as in Example 1 and terminated when the acid number reached 142.3 mgKOH/g (138.4 mgKOH/g in theory.)

After the reaction, the product was washed with water to remove unreacted acetic anhydride and acetic acid produced as a reaction by-product. A 200 g portion of the crude reaction mixture was dissolved in 200 g of ethyl acetate. This solution was washed with water four times using 400 g of water each time. After washing, ethyl acetate and a trace amount of water contained in the organic layer were removed by suction first with an aspirator (70–80 mmHg) for 1 hour and then a vacuum pump (5–10 mmHg) for 30 minutes.

EXAMPLE 6

A four necked 1L flask equipped with an air tube, thermometer, condenser, stirrer and separater was charged with 274.2 g of Material A, 135.1 g of methyl acetate, 200 g of toluene and 4.0 g of p-toluenesulfonic acid. The mixture was allowed to react at 105°–110° C. for 15 hours. Methanol formed by the reaction was removed from the reaction system by distillation with the solvent and the solvent recoverd was returned to the reaction system. The reaction was terminated when methanol was no longer produced. After the reaction, the crude reaction mixture was washed twice with 10% sodium hydroxide solution using 150 g of the solution each time. After washing, toluene and a trace amount of water were removed from the organic layer by suction first with an aspirator (70–80 mgHg) for 1 hour and then a vacuum pump (5–10 mmHg) for 30 minutes.

We claim:

1. An acrylic monomer of the formula I:

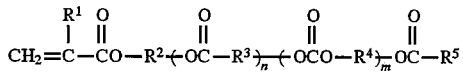

wherein $R^1$ is hydrogen or methyl, $R^2$ is a $C_2$-$C_8$-alkylene bridge, $R^3$ is a 1,5-pentylene bridge, $R^4$ is a 2,2-dimethyl-1,3-propylene bridge, $R^5$ is the residue of a monobasic $C_1$-$C_7$ alkanoic acid with removal of the carboxyl group or the residue of an aliphatic, alicyclic or aromatic dicarboxylic acid with removal of one of the carboxyl groups, n is zero or an integer of from 1 to 6, and m is an integer of from 1 to 6.

2. The acrylic monomer of claim 1, wherein n is an integer from 1 to 6.

3. The acrylic monomer of claim 1, wherein $R^5$ is the residue of a monobasic $C_1$-$C_7$ alkanoic acid with removal of the carboxyl group.

4. The acrylic monomer of claim 3, wherein the monobasic $C_1$-$C_7$ alkanoic acid is formic, acetic, propionic, butyric, valeric or caproic acid.

5. The acrylic monomer of claim 1, wherein $R^5$ is the residue of an aliphatic, alicyclic or aromatic dicarboxylic acid with removal of one of the carboxyl groups.

6. The acrylic monomer of claim 3, wherein the dicarboxylic acid is succinic, glutaric, tetrahydrophthalic, 3- or 4-methyltetrahydrophthalic or phthalic acid.

* * * * *